United States Patent [19]

Berris et al.

[11] Patent Number: 5,003,100

[45] Date of Patent: Mar. 26, 1991

[54] METHOD OF PRODUCING POLYSILANE COMPOUNDS

[75] Inventors: Bruce C. Berris; Steven P. Diefenbach, both of Baton Rouge, La.

[73] Assignee: Ethyl Corporation, Richmond, Va.

[21] Appl. No.: 548,488

[22] Filed: Jul. 3, 1990

[51] Int. Cl.$^5$ .................................. C07F 7/08
[52] U.S. Cl. .................................. 556/430; 528/15
[58] Field of Search .................... 556/430; 528/15

[56] References Cited

U.S. PATENT DOCUMENTS 4,590,253  5/1986  Hasegawa et al. ............. 556/430 X
4,820,788  4/1989  Zeigler .......................... 556/430 X
4,889,904  12/1989  Burns ............................ 556/430 X Primary Examiner—Paul F. Shaver
Attorney, Agent, or Firm—Terry B. Morris

[57] ABSTRACT

Improved methods for producing silanes using phosphorous rhodium dimer catalysts.

19 Claims, No Drawings

METHOD OF PRODUCING POLYSILANE COMPOUNDS

This invention relates to methods of producing polysilane compounds by the polymerization of monomeric or oligomeric silane precusor material in the presence of diphosphorous dimer catalysts.

BACKGROUND

Polysilane compounds have been produced heretofore by the reaction of dichlorosilane with metallic sodium. In these processes the silane has two R groups wherein R each represents hydrogen or hydrocarbon group, but not both R's are hydrogen at the same time. However, the method disadvantageously needs two moles of metallic sodium per mole of monomeric silane compound, and the use of metallic sodium in large amounts may not be feasible in the industrial production of polysilane compounds since, for example, sodium is readily combustible. Also, sodium tends to agglomerate during reactions. This can cause binding in agitators used to mix the reactants. The agglomerates size is difficult in size causing quality problems in the product. Moreover, the thus produced polysilane compound tends to contain residual chloride ions which adversely affect the electrochemical properties of the polymer.

J. Am. Chem. Soc., 108, 4059 (1986) proposed a method in which a phenylsilane is polymerized in the presence of an organotitanium complex to produce an $(RSiH_2)_m(RSiH)_n$ compound wherein n is about six and m is 0 or 2.

J. Organometal Chem., 55 (1973), C7-C8, described the heating of a monomeric hydrosilane compound in the presence of an organorhodium complex, $(Ph_3P)_3RhCl$, which provides oligomers such as dimers or trimers of the hydrosilane together with a significant amount of disproportionation products. The disproportion product contaminates the desired polysilane compound and can not be readily removed from the polysilane compound.

U.S. Pat. No. 4,900,861 discloses that organocomplexes of nickel, cobalt, ruthenium, palladium and iridium are effective as a catalyst for the polymerization of a monomeric silane compounds to produce higher molecular weight polysilane compound with substantially no by-products of undesired disproportionation products.

There remains a need for improved methods of polymerizing silane and polysilane precursive material to produce polysilane compounds.

SUMMARY

Improved methods have now been discovered for producing polysilane compounds. These methods include the use of phosphorus rhodium dimer catalysts. The catalysts used provide increased activity requiring less catalyst. Additionally they provide faster reactions while using a lower phosphorous to rhodium ratio.

DESCRIPTION OF THE PREFERRED EMBODIMENTS

In one embodiment the present invention is a method for polymerizing a monomeric or polymeric silane precursor material to produce a polysilane compound. This method comprises polymerizing an appropriate monomeric or oligomeric silane precursor material in the presence of an effective amount of a rhodium dimer catalyst producing a polysilane compound having an average molecular weight of about 300 or more compound. Unexpectedly the dimer character of the rhodium catalyst provides enhanced activity and produces larger silane oligomers than previously attained.

The rhodium dimer catalysts used in the present invention are diphosphorous rhodium halide dimers. Preferred diphosphorous rhodium halide dimers are composed of monomer groups with one or more cyclic hydrocarbons attached to the phosphorous atom, e.g. haloarylphosphine rhodium dimers. One such preferred dimer catalyst is chlorobis(tricyclohexylphosphine) rhodium dimer, represented by the following formula:

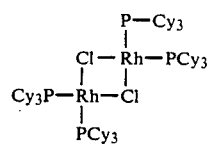

where Cy is cyclohexyl-, P is phosphorous, Rh is rhodium and Cl is chloride. This dimer catalyst is composed of the monomeric unit $(Cy_3P)_2RhCl$. Other preferred dimer catalysts have the monomeric units $(Cy_2PCH_2-)_2 RhCl$ and $(Ph_3P)_2RhCl$, wherein Ph is phenyl and $CH_2-$ is a methylene group linking the other methyl group attached to the other P phosphorous atom.

These dimer catalysts can be derived from precursor dimers, such as by using chlorobisethylene rhodium dimer. They are generally commercially available. The catalyst can be a chloride, but need not be restricted to a chloride with bromides and iodide also usuable, e.g. dimer form of the monomer $(Cy_2PCH_2-)_2RhBr$. Mixtures of halides may also be used. Likewise the alkyl ligand, if present, need not be restricted to methylene but can be any suitable alkyl group compatible with any solvent which might be present, e.g. a $C_1$ to about $C_6$ linear or branched group such as $(Cy_2PCH_2CH_2-)_2RhBr$. Likewise, another cyclic group, e.g. phenyl, can be used in place of the cyclohexyl group.

The dimer catalyst structure can have a ten-fold increase in activity on a weight basis over other known catalysts such as monomeric $(Ph_3P)_3RhCl$ and $Cp_2ZrMe_2$ (where Me is methyl, Zr is zirconium and Cp is cyclopentadiene). Likewise, the present catalyst has a phosphorous to rhodium ratio of two to one compared to prior art ratios of three to one, thereby requiring less phosphorous and, accordingly, less expensive catalyst. The dimer catalysts can produce a nearly quantitative yield of products with molecular weights of at least about 80, preferably at least about 300 and more preferably in the range of about 1000 to about 1500 depending upon desired end product.

In accordance with the invention, there is provided a method of producing a polysilane compound which comprises polymerizing a monomeric silane compound represented by the general formula

wherein R independently represents hydrogen or hydrocarbon group, but not both R's are hydrogen at the same time. When only one R is hydrogen, the compound can be represented by the formula RSiH₃.

Alternatively, an oligomeric compound can be used instead of the monomeric silane. The oligomeric silane compound used in the invention can be a polymeric silane precusor material, e.g. a silane polymer, which by example can be represented by the general formula of

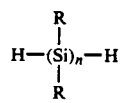

wherein R independently represents hydrogen or a hydrocarbon group, but not both R's are hydrogen at the same time, and n can range from about 2 to about 6. These precursor materials can be linear, branched or cyclic.

The product formed using either a monomeric or oligomeric silane precursor material can be either a linear, branched or cyclic polysilane. There need not be the same character of being linear, branched or cyclic for the precusive material as there is in the product, but there can be.

The R group for either monomeric or oligomeric silane units is a hydrocarbon group such that the silane unit is preferably either alkylsilane, arylsilane, dialkylsilane, diarylsilane or alkylarylsilane, in which the alkyl is preferably of one to about ten carbons and the aryl is preferably of about six to about fourteen carbons. More preferably the R group is phenyl, phenylalkyl (e.g., benzyl or phenethyl), alkylphenyl (e.g., tolyl or xylyl) or halophenyl (e.g. chlorophenyl or dichlorophenyl). The R group can be linear, branched or cyclic in structure, or a combination of such characters.

Thus, the monomeric silane compound used in the invention may be exemplified by alkylsilanes such as methylsilane, ethylsilane, n-propylsilane, isopropylsilane, n-butylsilane, n-pentylsilane, n-hexylsilane or n-heptylsilane; aryl silanes such as phenylsilane, benzylsilane or phenethylsilane; dialkylsilanes such as dimethylsilane, methylethylsilane, di-ethylsilane, methyl-n-propylsilane, methylisopropylsilane, ethyl-n-propylsilane, ethylisopropylsilane, diisopropylsilane, di-n-butylsilane or di-n-pentylsilane; alkylarylsilanes such as methylphenylsilane, ethylphenylsilane; or diarylsilanes such as diphenylsilane, phenyl-o-tolylsilane, phenyl-p-tolylsilane, phenyl-m-tolylsilane, phenyl-p-chlorophenylsilane, phenyl-2,4-dimethylphenylsilane or phenyl-2,4-dichlorophenylsilane. The monomeric silane compound may be used singly or as a mixture of two or more of such monomeric silanes. Further, if desired, oligomers, preferably dimers or trimers, of the monomeric silane compounds may be used in place of the monomeric silanes or together therewith.

The preferred monomeric silane compound used in the invention is phenylsilane, methylphenylsilane, diphenylsilane, ethylphenylsilane or hexylsilane, with phenylsilane, methylphenylsilane or diphenylsilane most preferred. These characterizations of the R groups for the silane units apply to both reactants and product silanes.

One product produced by the present invention are linear structure polysilane compounds.

The linear structure polysilane compound may be represented by

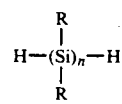

wherein R is the same as before, and n is an integer of not less than two, usually in the range of from two to about twenty. Preferably, n has a value of at least about ten.

Branched structure polysilane compounds can also be produced. When disubstituted silanes, e.g. diethylsilane or diphenyl silane, are allowed to react in the presence of the present catalyst, the product is the dehydrodimer 1,1,2,2-tetraethyldisilane or 1,1,2,2-tetraphenyldisilane, respectively.

The branched structure polysilane compounds have a silane branch through a Si-Si bond. An exemplified polysilane compound of the branched structure is as follows:

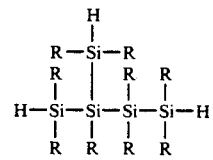

In addition to the linear or branched polysilane, it is possible that cyclic polysilane are produced. The cyclic structure polysilane compounds are represented by:

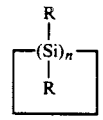

wherein R and n are as previously described.

In the method of the invention, the polymerization of the monomeric silane compound is carried out usually at temperatures in the range of from about −20° C. to about 80° C., preferably from about 20° C. to about 50° C. The reaction time may be in the range of from about 10 minutes to about 2 days. The reaction time is preferably from about 1 hour to 1 day. These reaction times depend upon the reaction temperature employed. The higher the temperature, the less reaction time is required.

Usually the reaction is carried out in the absence of a solvent, but may be carried out preferably in the presence of an inert solvent inactive to the reaction, if necessary. The solvents include, for example, aromatic hydrocarbons such as benzene or toluene, ethers such as methyl ethyl ether, diethyl ether, tetrahydrofuran or dioxane, acid amides such as dimethylformamide, or acid esters such as ethyl acetate or butyl acetate.

The amount of catalyst employed in the reaction is usually from about 0.0001 mole to about 0.5 moles, preferably from about 0.005 moles to about 0.05 moles, per mole of the monomeric or oligomeric silane compound used.

It is desired that the reaction be carried out under an inert gas atmosphere such as nitrogen or argon. The progress of the reaction is confirmed by evolution of hydrogen gas from the reaction mixture.

According to the invention, the monomeric silane compound polymerizes readily in the presence of the catalyst to provide polysilane compounds in high yields with substantially no undesired disproportionation products.

The invention will now be described with reference to experimental examples, which are, however, illustrative only, and the invention is not limited to the examples.

PRODUCTION OF DICHLOROBIS(TRICYCLOHEXYLPHOSPHINE)-RHODIUM DIMER CATALYST 0.25 grams (0.643 mmoles) chlorobis(ethylene) rhodium dimer was dissolved in 10 ml reagent grade toluene at room temperature and under an argon atmosphere. 0.720 grams (2.57 mmoles) tricyclohexylphosphine was added to form a mixture which was then stirred. Reflux of the mixture was performed at about 110 degrees centigrade under nitrogen for three hours. The mixture was then allowed to cool. After cooling, the mixture was filtered to remove solid contaminants. Hexane was added to the remaining liquid filtrate to form another mixture. The mixture was allowed to crystallize, forming yellow and orange crystals. The mother liquor from the crystallization was decanted off and the collected crystals were dissolved in toluene in which the orange material was slower to dissolve. The solution was filtered to remove the orange material before substantial dissolution of the orange material occurred. Then three volumes of hexane were added to the remaining material. Slow evaporation of the solution was performed to yield yellow crystals. The solution was decanted of the remaining liquid to recover the yellow material before appearance of any orange material. The collected material was dried. NMR showed fairly pure material.

The following elemental analysis of the collected material was determined:

|   | Calculated | Found |
|---|---|---|
| C | 61.84 | 62.13 |
| H | 9.51 | 9.57 |
| Cl | 5.07 | 4.17 |
| P | 8.86 | 8.65 |

The balance of the elements was presumed to be essentially rhodium.

POLYMERIZATION OF HEXYLSILANE USING RHODIUM DIMER CATALYST 5 mgs. of the above prepared rhodium dimer catalyst was mixed with 1.00 grams of hexylsilane at room temperatures in an open vial under argon. Hydrogen began evolving immediately. The reaction was allowed to continue for about three days after which little or no further reaction was apparent. The product was subjected to GPC analysis which showed an oligomer molecular weight of 1380.

The following table provides the results of polymerizinq the listed silane monomers using different phosphorous rhodium dimer catalysts. The catalyst listings are the monomeric units for the dimers except for the catalysts $(Ph_3P)_3RhCl$ and $Cp_2ZrMe_2$, both of which were actually monomers. Each experiment was performed by stirring 10 to 20 milligrams of catalyst together with 1 gram of the silane monomer in an open vial under argon for one to two days at room temperatures.

| Catalyst | Silane Monomer | Product | Molecular Weight |
|---|---|---|---|
| $(Cy_2PCH_2-)_2RhCl$ | hexyl | oligomer | 750 |
|  | phenyl | oligomer | 340 |
| $(Cy_3P)_2RhCl$ | hexyl-1st day | oligomer | 1100 |
|  | hexyl-2nd day | oligomer | 1150 |
|  | hexyl-3rd day | oligomer | 1380 |
| $(Ph_3P)_2RhCl$ | diphenyl | dimer |  |
|  | hexyl | oligomer | 570 |
|  | hexyl-1st day | oligomer | 870 |
|  | hexyl-2nd day | oligomer | 710 |
| $(Ph_3P)_3RhCl$ | hexyl | dimer/trimer mixture |  |

What is claimed is:

1. A method for polymerizing a monomeric or oligomeric silane precursor material to produce a polysilane compound comprising polymerizing said monomeric or polymeric silane precursor material in the presence of an effective amount of a diphosphorous rhodium dimer catalyst for producing an average molecular weight of about 300 or more for said polysilane compound.

2. The method of claim 1 wherein the monomeric silane precursor is $RSiH_3$ and R is an alkyl, aryl, or alkylaryl group.

3. The method of claim 2 wherein said $RSiH_3$ is an alkyl $SiH_3$.

4. The method of claim 3 wherein said alkyl $SiH_3$ has from one to about ten carbon atoms.

5. The method of claim 4 wherein the alkyl group of the alkyl $SiH_3$ is a linear alkyl.

6. The method of claim 5 wherein the linear alkyl group is methyl, ethyl or n-propyl.

7. The method of claim 2 wherein R of $RSiH_3$ is phenyl or methylphenyl.

8. The method of claim 1 wherein the monomeric silane precursor is $R_2SiH_2$ and each R is independently either an alkyl, aryl or alkylaryl group.

9. The method of claim 1 wherein said polysilane compound is linear.

10. The method of claim 1 wherein said polysilane compound has from about two to about twenty silane atoms.

11. The method of claim 1 wherein said polysilane compound has at least ten silane atoms.

12. The method of claim 11 wherein said average molecular weight is from at least about 1000 to about 1500.

13. The method of claim 1 wherein the diphosphorous rhodium dimer catalyst comprises one or more cyclic hydrocarbons attached to a phosphorus atom.

14. The method of claim 13 wherein said diphosphorous rhodium dimer is haloarylphosphine rhodium dimer.

15. The method of claim 14 wherein the halogen group of the haloalkylphosphine is bromine, chlorine or iodine.

16. The method of claim 15 wherein the catalyst is the dimer of $(Cy_2PCh_2—)_2RhCl$.

17. The method of claim 15 wherein the catalyst is the dimer of $(Cy_3P)_2RhCl$.

18. The method of claim 15 wherein the catalyst is the dimer of $(Ph_3P)_2RhCl$.

19. A polysilane compound having an average molecular weight of about 200 or more produced by the process comprising polymerizing said monomeric or polymeric silane precursor material in the presence of an effective diphosphorous rhodium dimer catalyst for producing an average molecular weight of about 300 or more for said polysilane compound.

* * * * *

UNITED STATES PATENT AND TRADEMARK OFFICE
CERTIFICATE OF CORRECTION

PATENT NO. : 5,003,100

DATED : March 26, 1991

INVENTOR(S) : BRUCE C. BERRIS AND STEVEN P. DIEFENBACH

It is certified that error appears in the above-identified patent and that said Letters Patent is hereby corrected as shown below:

On the title page, "19 Claims, No Drawings" should read --18 Claims, No Drawings--.

Delete Claim 19, which is contained in Column 6, Lines 61-67

Signed and Sealed this

Twenty-fifth Day of August, 1992

*Attest:*

DOUGLAS B. COMER

*Attesting Officer*   *Acting Commissioner of Patents and Trademarks*